United States Patent [19]

Wilk

[11] Patent Number: 5,409,019
[45] Date of Patent: * Apr. 25, 1995

[54] CORONARY ARTERY BY-PASS METHOD

[76] Inventor: Peter J. Wilk, 185 West End Ave., New York, N.Y. 10023

[ * ] Notice: The portion of the term of this patent subsequent to Feb. 22, 2011 has been disclaimed.

[21] Appl. No.: 147,072

[22] Filed: Nov. 3, 1993

Related U.S. Application Data

[63] Continuation-in-part of Ser. No. 969,747, Oct. 30, 1992, Pat. No. 5,287,861.

[51] Int. Cl.$^6$ .............................................. A61B 17/00
[52] U.S. Cl. ................................... 128/898; 128/673; 600/16
[58] Field of Search .................... 128/897–898, 128/672–673, 748, 772, 774; 600/16–18; 606/7; 604/96, 100, 104

[56] References Cited

U.S. PATENT DOCUMENTS

| | | | |
|---|---|---|---|
| 3,995,617 | 12/1976 | Watkins et al. | 600/16 |
| 4,546,499 | 10/1985 | Possis et al. | 623/1 |
| 4,562,597 | 1/1986 | Possis et al. | 623/1 |
| 4,861,330 | 8/1989 | Voss | 600/18 |
| 4,953,553 | 9/1990 | Tremulis | 128/673 |
| 4,985,014 | 1/1991 | Orejola | 600/16 |
| 4,995,857 | 2/1991 | Arnold | 600/16 |
| 5,143,093 | 9/1992 | Sahota | 128/898 |
| 5,190,058 | 3/1993 | Jones et al. | 128/898 |
| 5,287,861 | 2/1994 | Wilk | 128/673 X |

*Primary Examiner*—Angela D. Sykes
*Attorney, Agent, or Firm*—R. Neil Sudol; Henry D. Coleman

[57] ABSTRACT

A coronary-bypass method uses a collapsible stent made of a biocompatible material and having an inherent spring bias tending to form the stent into a substantially tubular opened configuration. The stent is disposed in a wall of a patient's heart so that the stent extends between the left ventricle of the heart and a coronary artery. Upon placement, the stent opens and allows blood to flow from the left ventricle into the coronary artery during diastole and is closed by heart contraction during systole.

18 Claims, 4 Drawing Sheets

CORONARY ARTERY BY-PASS METHOD

CROSS-REFERENCE TO RELATED APPLICATION

This application is a continuation-in-part of U.S. Patent application Ser. No. 07/969,747 filed Oct. 30, 1992, now U.S. Pat. No. 5,287,861.

BACKGROUND OF THE INVENTION

This invention relates to a method for effectuating a coronary artery bypass.

Coronary arteries frequently become clogged with plaque which at the very least impairs the efficiency of the heart's pumping action and can lead to heart attack. The conventional treatment for a clogged coronary artery is a coronary by-pass operation wherein one or more venous segments are inserted between the aorta and the coronary artery. The inserted venous segments or transplants by-pass the clogged portion of the coronary artery and thus provide for a free or unobstructed flow of blood to the heart.

Such conventional coronary artery by-pass surgery is expensive, time-consuming, and traumatic to the patient. Hospital stay subsequent to surgery and convalescence are prolonged.

OBJECTS OF THE INVENTION

An object of the present invention is to provide a new method for performing a coronary artery by-pass operation.

Another object of the present invention is to provide such a method which is less invasive and less traumatic to the patient than conventional by-pass surgery.

An additional object of the present invention is to provide such a method which is less expensive than conventional by-pass surgery.

A more particular object of the present invention is to provide such a method which requires no incision through the chest wall.

Yet another object of the present invention is to provide a catheter assembly for use in performing the method of the invention.

These and other objects of the present invention will be apparent from the drawings and detailed descriptions herein.

SUMMARY OF THE INVENTION

A cardiovascular treatment method comprises, in accordance with the present invention, the steps of (a) providing a stent made of a biocompatible material, (b) moving the stent in a collapsed configuration through a blood vessel of a patient's vascular system to a coronary artery, and (c) upon the disposition of the stent in the coronary artery, disposing the stent in a wall of the patient's heart so that the stent extends between the left ventricle of the heart and the coronary artery and extends only within the wall and not into the left ventricle or the coronary artery. Upon the disposition of the stent in the heart wall, the stent is expanded from the collapsed configuration to a substantially tubular expanded configuration so that a flow path is formed from the left ventricle to the coronary artery.

Pursuant to another feature of the present invention, the disposition of the stent in the heart wall includes the steps of inserting a catheter into the clogged coronary artery and ejecting the stent from a distal end of the catheter into the heart wall.

Preferably, a perforation is formed in the heart wall prior to the ejection of the stent from the catheter. The perforation or opening may be formed by ejecting a needle into the heart wall from the distal end of the catheter and/or pushing a rotating drill head into the heart wall from the distal end of the catheter.

The formation of the perforation in the heart wall and the ejection of the stent into the perforation may be more easily implemented during diastole. In that event, a computer may be operated to synchronize the perforation formation and the stent ejection with the rhythm of the heart.

Pursuant to another feature of the present invention, a collapsed inflatable balloon may be ejected or inserted with the stent into the heart wall from the distal end of the catheter. The stent surrounds the balloon. The balloon is then inflated and the stent expanded upon ejection of the balloon and the stent into the heart wall.

Pursuant to yet another feature of the present invention, the balloon and the stent are inserted into the heart wall over a guide wire, the method further including the step of inserting the guide wire into the perforation in the heart wall prior to the ejection of the collapsed balloon and the stent from the distal end of the catheter.

A coronary artery by-pass method in accordance with the present invention may also comprise the steps of (a) inserting a distal end portion of the catheter into the perforation in the heart wall prior to the ejection of the stent, (b) sensing pressure on the catheter along the distal end portion, thereby determining a thickness of the heart wall at the perforation, and (c) cutting the stent from a piece of stent material so that the stent has a length corresponding to the thickness of the heart wall at the perforation.

According to another feature of the present invention, the stent has an inherent spring bias tending to form the stent into the opened configuration. In that case, the method in accordance with the present invention further comprises the steps of (i) opening the stent and thereby allowing blood to flow from the left ventricle into the coronary artery during diastole and (ii) closing the stent by heart contraction during systole.

Alternatively, the stent is provided with a one-way valve. In that event, the expanded stent is maintained in an expanded state during both diastole and systole. Blood flows from the left ventricle into the coronary artery through the stent during systole and is blocked from returning into the left ventricle through the stent during diastole.

A method for supplying blood to the heart comprises, in accordance with another conceptualization of the present invention, the steps of (1) forcing blood from the left ventricle of the heart during systole and directly into a coronary artery through a stent disposed in a wall of the heart and (2) closing a valve in the stent during diastole to block a return of blood from the coronary artery into the left ventricle.

A method in accordance with the present invention greatly reduces the expense of coronary surgery, as well as the trauma to the patient and the convalescence required after the by-pass operation. A coronary artery by-pass operation in accordance with the present invention may be performed by a radiologist, through the vascular system of the patient. Accordingly, only one or two small incisions in the patient are necessary.

DETAILED DESCRIPTION

Figure 1:
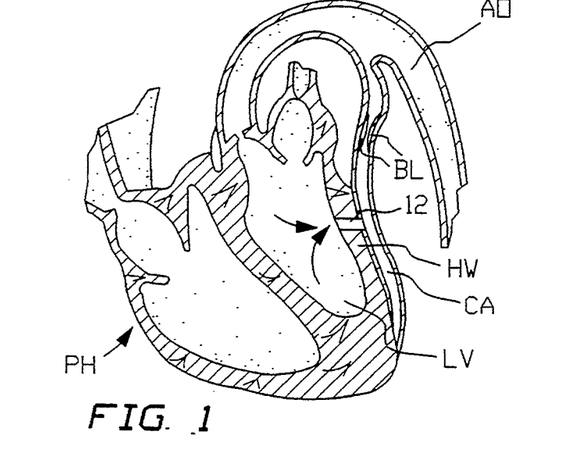
FIG. 1 is a schematic cross-sectional view of a human heart, showing a stent in the wall of the heart for forming a bypass shunt between the left ventricle and a coronary artery, in accordance with the present invention.
Figures 2A, 2B, 3A:
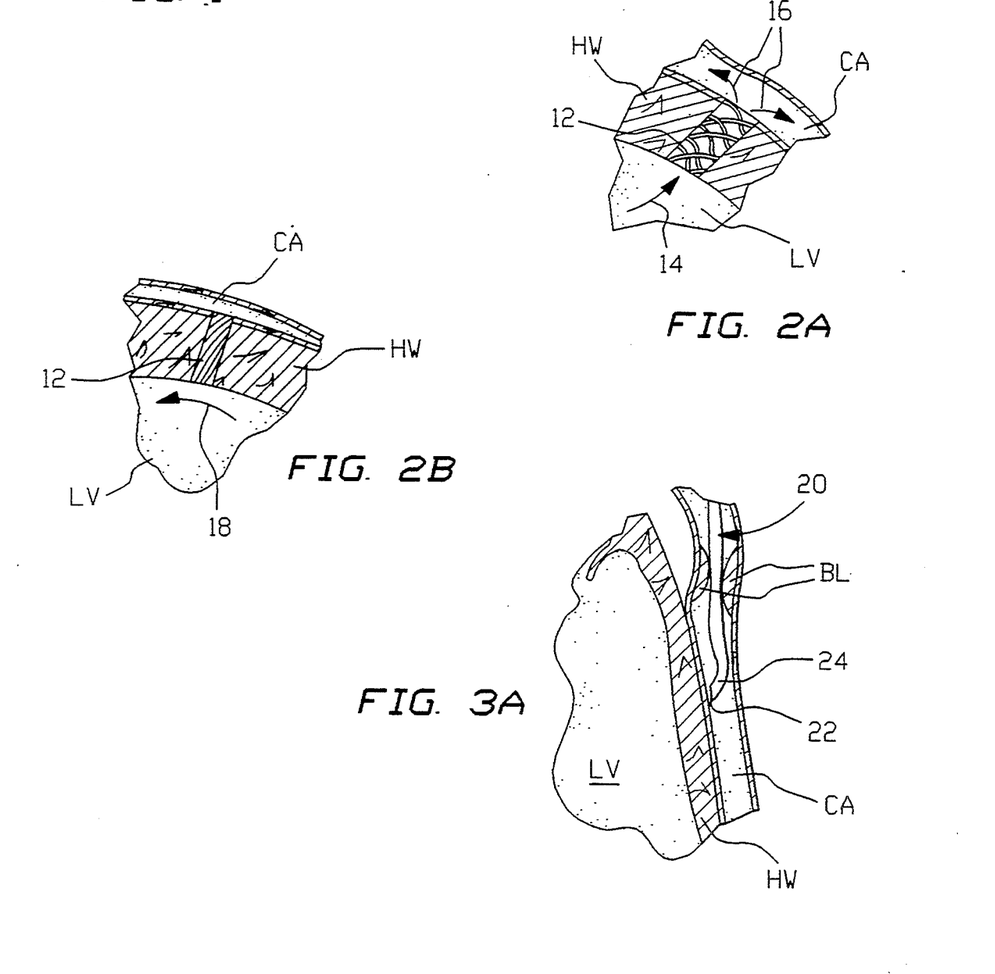
FIG. 2A is a partial cross-sectional view, on a larger scale, showing the stent of FIG. 1 in an opened or expanded configuration allowing blood flow into the coronary artery during diastole.
FIG. 2B is a partial cross-sectional view similar to FIG. 2A, showing the stent in an closed configuration blocking blood flow between the ventricle and the coronary artery during systole.
FIGS. 3A-3E are partial cross-sectional views showing successive steps in the implantation of a stent in a method in accordance with the present invention.

As illustrated in FIG. 1, a coronary artery by-pass is accomplished by disposing an alternately collapsible and expandable stent 12 in a wall HW of a patient's heart PH. Stent 12 extends from the left ventricle LV of heart PH to a clogged coronary artery CA at a point downstream of a blockage BL. Stent 12 is made of a biocompatible material and has an inherent spring bias or memory tending to form the stent into a substantially tubular opened configuration (FIG. 2A) during the relaxation of the surrounding heart muscle during the diastolic phase of a cardiac cycle. Stent 12 thus opens a passageway between ventrical LV and artery CA during diastole to allow blood to flow from the ventricle into the artery, as indicated by arrows 14 and 16 in FIG. 2A. Upon contraction of the surrounding heart muscle in the systolic phase of a cardiac cycle, stent 12 is forced closed, thus blocking or preventing blood flow between ventricle LV and coronary artery CA, as represented by an arrow 18 in FIG. 2B. FIG. 2A shows coronary artery CA in a partially collapsed configuration characteristic of diastole. Other drawing figures herein show coronary artery CA expanded for purposes of illustration simplification and clarity.

As illustrated in FIG. 3A, implantation or disposition of stent 12 in heart wall HW begins with the insertion of a catheter 20 through the aorta AO (FIG. 1) and into coronary artery CA. In artery CA, catheter 20 is forced past blockage BL so that the distal tip 22 of catheter 20 is disposed in a desired location opposite heart wall HW. Catheter 20 has a steerable tip, as discussed more fully hereinafter with reference to FIG. 4, so that distal tip 22 may be controllably oriented to face wall HW, as indicated in FIG. 3A.

Figure 3B:
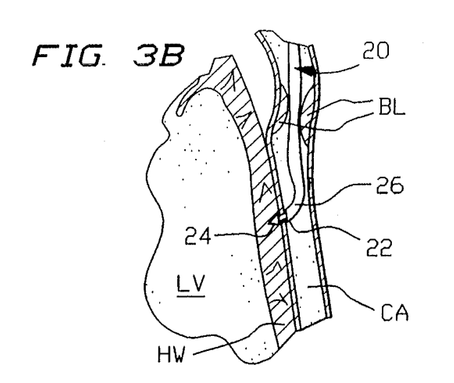
Figure 3C:
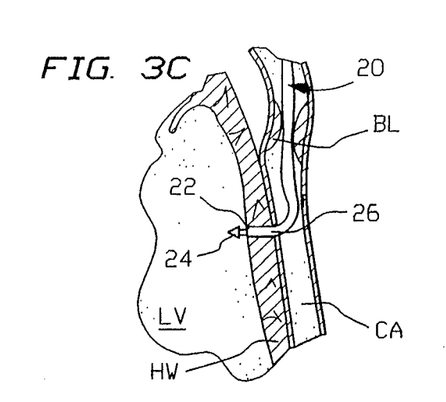

Upon a bringing of distal tip 22 into contact with wall HW, a rotary head 24 of a surgical drill is ejected from distal tip 22, as shown in FIG. 3B. Head 24 is rotated during a pushing of catheter 20 in the distal direction, thereby forming a perforation or passage in heart wall HW. A distal end portion 26 of catheter 20 including tip 22 is inserted into the perforation in the heart wall HW during the formation of the perforation by drill head 24, as depicted in FIG. 3C.

Upon the disposition of distal end portion 26 of catheter 20 in heart wall HW, the surgical drill is withdrawn from the catheter. Stent 12 is then inserted in a collapsed configuration down catheter 20. A push rod (not shown) may be used to position stent 12 in distal end portion 26 of catheter 20 so that the stent is coextensive with heart wall HW.

Figure 3D:
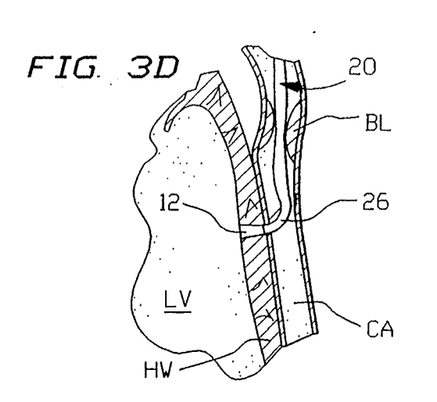
Figure 3E:
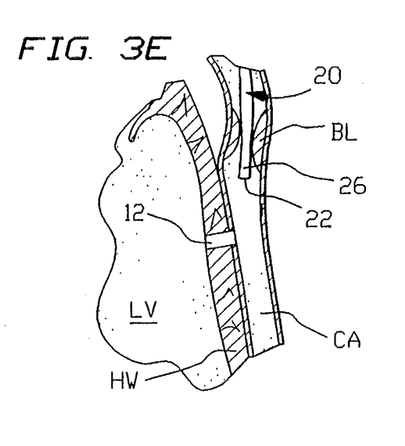

Upon the positioning of stent 12 in a collapsed configuration inside distal end portion 26 of catheter 20, catheter 20 is withdrawn from heart wall HW, while stent is maintained in position relative to heart wall. Upon the consequent ejection of stent 12 from distal tip 22 of catheter 20, as illustrated in FIG. 3D, stent 12 automatically expands from its collapsed configuration, provided that heart PH is in a diastolic phase of a cardiac cycle. Subsequently to the completed ejection of stent 12 from catheter 20, catheter 20 is withdrawn, as illustrated in FIG. 3E.

Figure 4:
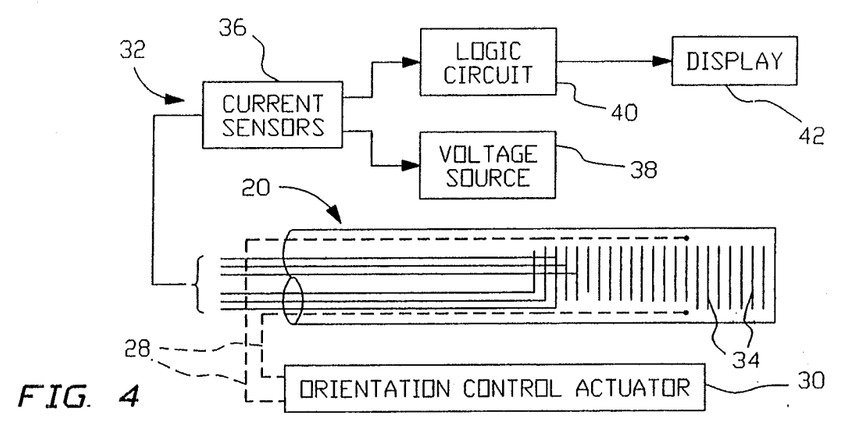
FIG. 4 is partially a block diagram and partially a side elevational view on an enlarged scale of a catheter assembly in accordance with the present invention for use in executing a method in accordance with the present invention.

FIG. 4 shows an angioplastic surgical device for use in the method described above with reference to FIGS. 3A-3E. The device includes catheter 20 insertable into aorta AO and coronary artery CA. Steering componentry including a plurality of wires 28 and an orientation control actuator 30 is connected to catheter 20 for enabling an operator to control, from outside the patient, an orientation of distal tip 22 of catheter 20 upon insertion of the catheter into the patient. A pressure sensor assembly 32 is operatively connected to catheter 20 for measuring the length of distal end portion 26 which is coextensive with heart wall HW upon completion of the catheter insertion (FIG. 3C). Pressure sensor assembly 32 may include a multiplicity of strain gauges 34 embedded in distal end portion 26, the strain gauges being connected to a current sensor array 36 and a voltage source 38. Current sensor array 36 is in turn connected to a logic circuit 40 which determines the length of that portion of catheter 20 at a distal end thereof which is subjected to increased compressive pressure especially during the systolic phase of the cardiac cycle. Circuit 40 is connected to a display 42 by means of which the thickness of the heart wall HW is communicated to a surgeon or radiologist. Stent 12 may then be customized to the patient. The length of stent 12 is matched to the measured thickness of heart wall HW by cutting the stent from a provided stent segment. Alternatively, stent 12 may be selected from a kit of different stent sizes. Of course, the cutting of stent 12 or the selection thereof may be implemented automatically by a computer operated according to a numerical control program.

Figure 5A:
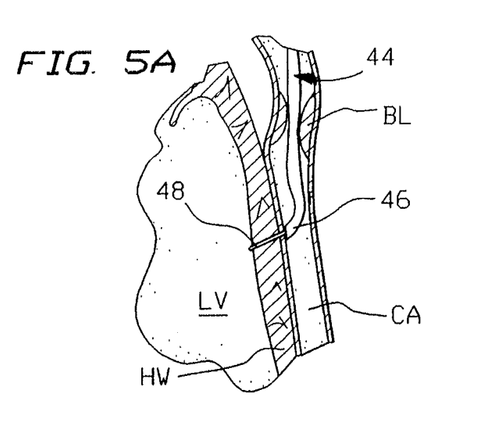
FIGS. 5A-5C are partial cross-sectional views showing successive steps in the implantation of a stent in another embodiment of a method in accordance with the present invention.
Figures 5B, 5C:
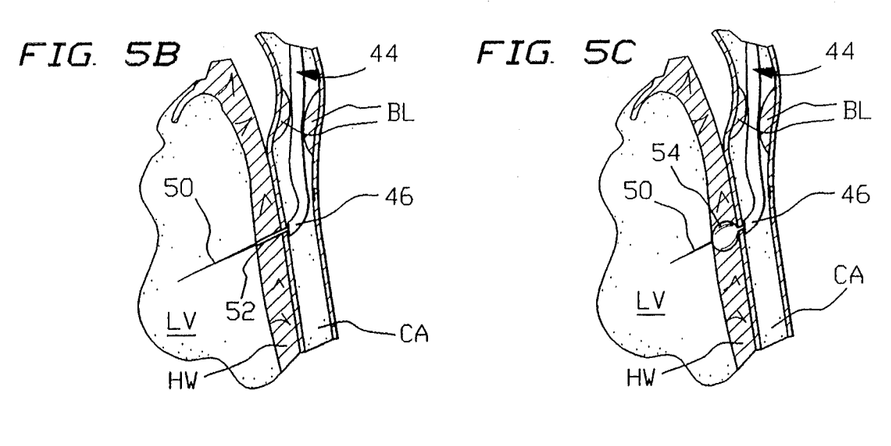

As illustrated in FIGS. 5A–5C, in another procedure for disposing stent 12 in heart wall HW, a catheter 44 with a steerable distal end 46 is maneuvered to position distal end 46 in coronary artery CA and to place the end of the catheter into contact with heart wall HW. A hollow needle 48 (FIG. 5A) is then ejected from distal end 46 of catheter 44 into heart wall HW, whereupon a Seldinger wire 50 (FIG. 5B) is moved in the distal direction through catheter 44 and needle 48. Upon the projection of the distal end of wire 50 from needle 48, needle 48 is withdrawn and an auxiliary catheter 52 (FIG. 5B) is inserted through catheter 44 and over wire 50. Catheter 52 is provided with a pressure sensor assembly (not shown), as discussed hereinabove with reference to FIG. 4, for measuring the thickness of heart wall HW.

Upon the measurement of the thickness of heart wall HW, catheter 52 is withdrawn and a balloon 54 surrounded by stent 12 (not separately shown in FIG. 5C) is inserted through catheter 44 and over wire 50. Upon a positioning of balloon 54 and stent 12 inside heart wall HW, balloon 54 is inflated (FIG. 5C) to assist in an initial expansion of stent 12 in opposition to the compressive forces of the heart muscle. Upon the desired disposition of stent 12, balloon 54 and wire 50 and subsequently catheter 44 are withdrawn, leaving stent 12 in place as a coronary artery by-pass or shunt between ventricle LV and artery CA.

Figure 6A:
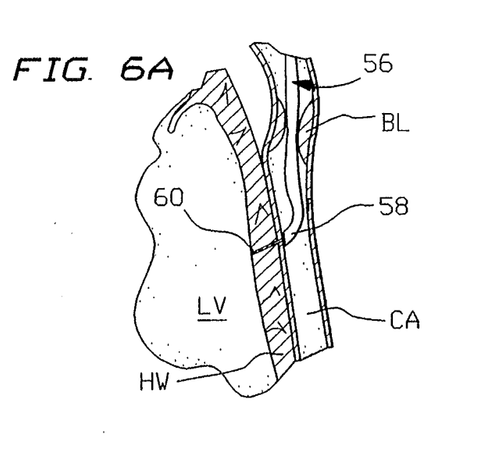
FIGS. 6A-6C are partial cross-sectional views showing successive steps in the implantation of a stent in yet another embodiment of a method in accordance with the present invention.
Figures 6B, 6C:
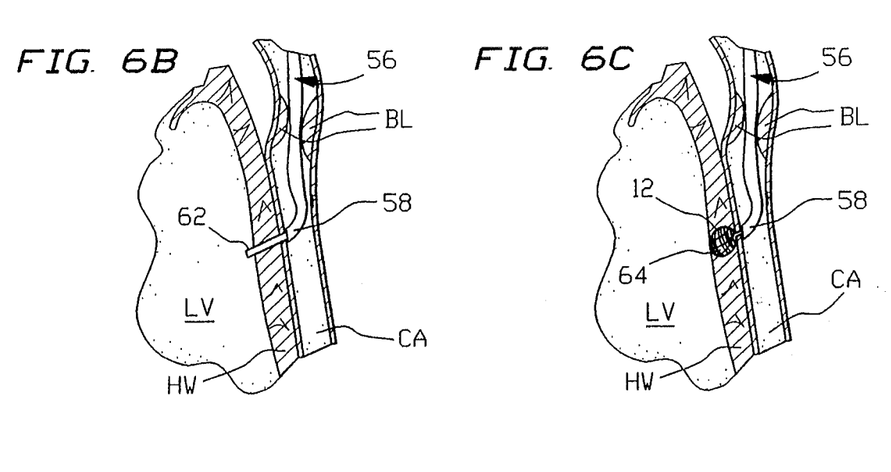

As illustrated in FIGS. 6A–6C, in another procedure for disposing stent 12 in heart wall HW, a catheter 56 with a steerable distal end 58 is maneuvered to position the distal end in coronary artery CA and to place the end of the catheter into contact with heart wall HW. A needle or wire 60 (FIG. 6A) is then ejected from distal end 58 of catheter 56 into heart wall HW, whereupon a series of dilating catheters 62 (FIG. 6B) of progressively increasing diameter are inserted in the distal direction through catheter 56 and over needle 60 into heart wall HW. Upon the ejection of a largest dilating catheter 62 from catheter 56 so that it traverses heart wall HW, the dilating catheter is withdrawn and a balloon 64 surrounded by stent 12 (FIG. 6C) is inserted through catheter 56 and over needle or wire 60. Upon a positioning of balloon 64 and stent 12 inside heart wall HW, balloon 64 is inflated (FIG. 6C) to assist in an initial expansion of stent 12 in opposition to the compressive forces of the heart muscle.

Upon the measurement of the thickness of heart wall HW, catheter 52 is withdrawn and a balloon 54 surrounded by stent 12 (not separately shown in FIG. 6C) is inserted through catheter 56 and over wire 50. Upon a positioning of balloon 54 and stent 12 inside heart wall HW, balloon 54 is inflated (FIG. 6C) to assist in an initial expansion of stent 12 in opposition to the compressive forces of the heart muscle. Upon the desired disposition of stent 12, balloon 54 and wire 50 and subsequently catheter 56 are withdrawn, leaving stent 12 in place as a coronary artery by-pass or shunt between ventricle LV and artery CA.

The disposition of a by-pass stent as described hereinabove may be implemented in part via a computer programmed to enable the timing of heart perforation, catheter or stent insertion, balloon inflation, and other operations so that those operations are performed only during the diastolic phase of a cardiac cycle. The programming and utilization of a computer in such a procedure will be clear to one skilled in the art from the teachings of U.S. Pat. No. 4,788,975 to Shturman et al., the disclosure of which is hereby incorporated by reference.

Figure 7A:
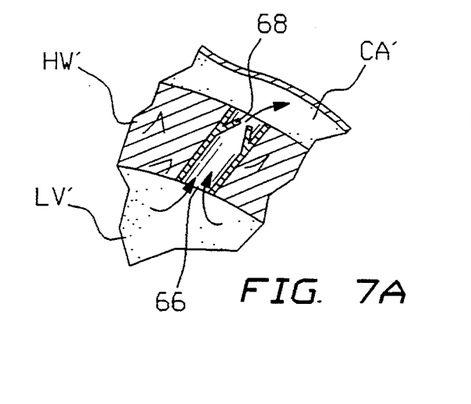
FIG. 7A is a partial cross-sectional view, similar to FIG. 2A, showing an operative configuration of another stent placed in a heart wall in accordance with the present invention, the stent having an opened one-way valve allowing blood flow into the coronary artery during systole.
Figure 7B:
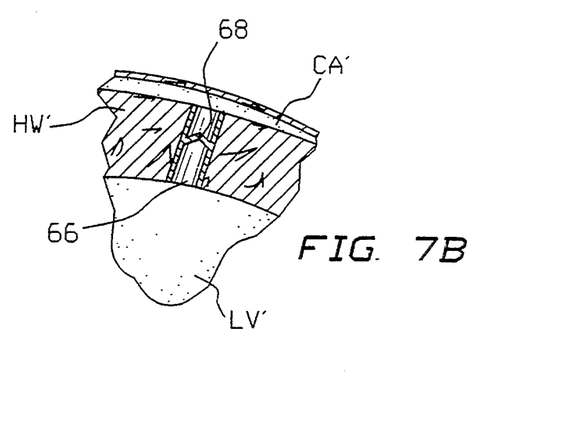
FIG. 7B is a partial cross-sectional view similar to FIG. 7A, showing the stent with the valve closed to block blood flow between from the coronary artery to the ventricle during diasystole.

As shown in FIGS. 7A and 7B, a coronary by-pass may be effectuated by disposing a stent 66 with a one-way valve 68 in a heart wall HW' of a patient. In accordance with the embodiment of FIGS. 7A and 7B, once stent 66 is positioned in heart wall HW', the stent remains in a substantially expanded configuration. Although the stent may elastically deform under the contractive pressure of the heart muscle during systole, the stent remains opened to allow blood to pass from the patient's left ventricle LV' into the coronary artery CA'. During diastole, the blood pumped into coronary artery through shunt 66 is blocked by one-way valve 68 from returning to left ventricle LV'.

Stent 66 is installed in the patient's heart via essentially the same procedure or procedures described hereinabove for inserting stent 12. The difference between the use of stent 12 and the use of stent 66 arises from their structure. Stent 12 is designed to collapse and close during systole, while stent 66 is designed to resist the contractive pressure of the heart and to remain opened during systole to permit the flow of blood through the stent into coronary artery CA'.

Figure 8A:
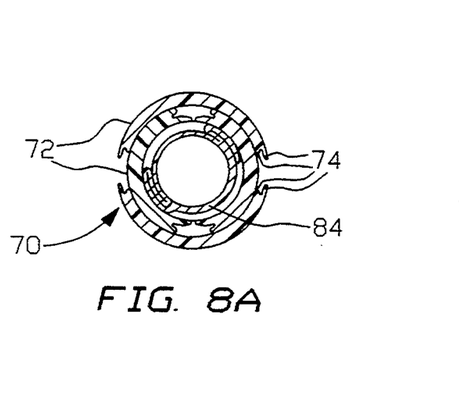
FIG. 8A is a schematic transverse cross-sectional view of another coronary by-pass stent in accordance with the present invention, showing the stent in a collapsed, pre-insertion configuration.
Figure 8B:
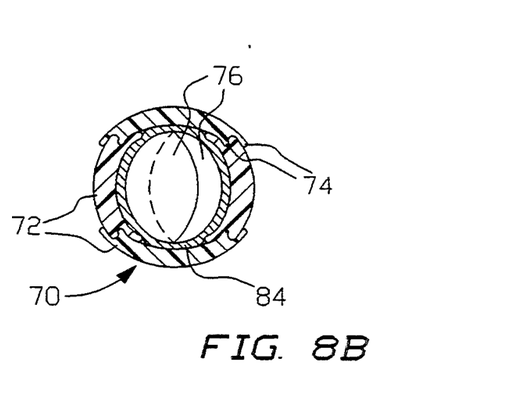
FIG. 8B is a schematic transverse cross-sectional view of of the coronary by-pass stent of FIG. 9A, showing the stent in an expanded collapsed, post-insertion configuration.

As illustrated in FIGS. 8A and 8B, a stent 70 designed to resist the contractive pressure of the heart and to remain opened during systole comprises a plurality of interlocking segments 72 which overlap one another in a collapsed insertion configuration of the s tent (FIG. 8A). Along their longitudinally or axially extending edges, stent segments 72 are provided with mating or interdigitating fingers 74. In the insertion configuration, the projections are spaced from one another. Upon insertion of stent 70 into the heart tissues and subsequent expansion of the stent by a balloon (not shown), fingers 74 slip into an interleaved configuration, thereby locking the stent in an opened tubular configuration which resists collapse during the systolic contractions of the heart.

Stent 70 is provided with valve flaps 76. Stent 70, like stent 12 and stent 66, is made of a biocompatible material. Valve flaps may be made of similar material in with a smaller thickness. It is to be noted that stents 66 and 70 may deform elastically during systole. Their lengths may increase during such deformation. However, they remain sufficiently open to allow the passage of blood from the left ventricle into the coronary artery.

Figure 9:
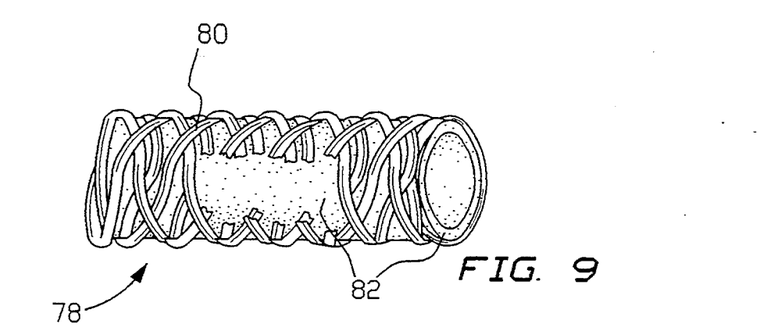
FIG. 9 is a schematic side perspective view, on an enlarged scale and partially broken away, of a modified coronary by-pass stent for use in a method in accordance with the present invention.

As illustrated in FIG. 9, a stent 78 for use in a bypass procedure as described hereinabove includes an outer layer 80 of interwoven helical strands of biocompatible material. An inner layer 82 is a vascular graft taken from the patient prior to the by-pass operation. Vascular graft layer 82 may be connected to outer layer 80, for example, by adhesive or laser welding. FIGS. 8A and 8B also show a vascular graft layer 84 inside stent segments 72. Where a graft lining is inserted in a stent with a valve, it may be necessary to insert two vascular graft sections into the prosthetic device from opposite ends thereof.

Although the invention has been described in terms of particular embodiments and applications, one of ordinary skill in the art, in light of this teaching, can generate additional embodiments and modifications without departing from the spirit of or exceeding the scope of the claimed invention. For example, other equivalent techniques may be used for measuring the thickness of heart wall HW or determining an appropriate length of stent 12. A "measuring rod" of a predetermined length may be inserted through the angioplastic catheter. A computer connected to a CAT-scanner, an MRI machine or other imaging device then automatically determine heart wall thickness by comparing the dimensions thereof to the known length of the "measuring rod."

It is to be noted that several stents in accordance with the present invention may be disposed in the heart wall of a single heart, thereby connecting the left ventricle to one or more points along a coronary artery or to several arteries during the diastolic phase of a cardiac cycle.

Accordingly, it is to be understood that the drawings and descriptions herein are profferred by way of example to facilitate comprehension of the invention and should not be construed to limit the scope thereof.

What is claimed is:

1. A cardiovascular treatment method comprising the steps of:
   providing a stent made of a biocompatible material;
   moving said stent in a collapsed configuration through a blood vessel of a patient's vascular system to a coronary artery;
   upon the disposition of said stent in said coronary artery, disposing said stent in a wall of the patient's heart so that said stent extends between the left ventricle of the heart and the coronary artery and extends only within said wall; and
   upon the disposition of said stent in said wall, expanding said stent from said collapsed configuration to a substantially tubular expanded configuration so that a flow path is formed from the left ventricle to the coronary artery.

2. The method defined in claim 1 wherein said step of disposing includes the steps of inserting a catheter into the coronary artery and ejecting said stent from a distal end of said catheter into said wall.

3. The method defined in claim 2 wherein said step of disposing further includes the step of forming a perforation in said wall prior to said step of ejecting.

4. The method defined in claim 3 wherein said step of disposing also includes the steps of ejecting a collapsed inflatable balloon with said stent into said wall from said distal end of said catheter, said stent surrounding said balloon, and inflating said balloon and opening said stent upon ejection of said balloon and said stent into said wall.

5. The method defined in claim 4 wherein said steps of inflating and opening are performed during diastole.

6. The method defined in claim 4 wherein said balloon and said stent are inserted into said wall over a guide wire, further including the step of inserting said guide wire into said perforation prior to the ejection of said collapsed balloon and said stent from said distal end of said catheter.

7. The method defined in claim 3, further comprising the steps of inserting a distal end portion of said catheter into said perforation prior to said step of ejecting, sensing pressure on said catheter along said distal end portion, thereby determining a thickness of said heart wall at said perforation, and cutting said stent from a piece of stent material so that said stent has a length corresponding to the thickness of said heart wall at said perforation.

8. The method defined in claim 3 wherein said step of forming includes the step of ejecting a needle into said wall from said distal end of said catheter.

9. The method defined in claim 3 wherein said step of forming includes the steps of pushing a drill head into said wall from said distal end of said catheter and rotating said drill head during said step of pushing.

10. The method defined in claim 3 wherein said steps of forming and ejecting are implemented during diastole.

11. The method defined in claim 3, further comprising the step of operating a computer to synchronize said steps of forming and ejecting with the rhythm of said heart.

12. The method defined in claim 1 wherein said stent has an inherent spring bias tending to form the stent into said opened configuration, further comprising the steps of opening said stent and thereby allowing blood to flow from said left ventricle into the coronary artery during diastole and closing said stent by heart contraction during systole.

13. The method defined in claim 1 wherein said stent is provided with a one-way valve, further comprising the steps of:
   maintaining said stent expanded in said opened configuration during both diastole and systole upon completion of said step of expanding;
   permitting flow from said left ventricle into said coronary artery through said stent during systole; and
   blocking flow from said coronary artery back into said left ventricle through said valve during diastole.

14. A method for supplying blood to the heart, comprising the steps of:
   during systole, forcing blood from the left ventricle of the heart and directly into a coronary artery through a stent disposed in a wall of the heart; and
   during diastole, closing a valve in said stent to block a return of blood from said coronary artery into said left ventricle.

15. A cardiovascular treatment method comprising the steps of:
   providing a stent made of a biocompatible material and provided with a one-way valve;
   moving said stent in a collapsed configuration through a blood vessel of a patient's vascular system to a coronary artery;
   upon the disposition of said stent in said coronary artery, disposing said stent in a wall of the patient's heart so that said stent extends between the left ventricle of the heart and the coronary artery and so that said one-way valve prevents flow from said coronary artery into said left ventricle, said stent being essentially coextensive with said wall upon disposition of said stent in said wall so that said stent extends only within said wall and does not extend into the left ventricle or the coronary artery; and
   upon the disposition of said stent in said wall, expanding said stent from said collapsed configuration to a substantially tubular permanently expanded configuration so that a flow path is formed from the left ventricle to the coronary artery.

16. The method defined in claim 15 wherein said step of disposing includes the steps of inserting a catheter into the coronary artery and ejecting said stent from a distal end of said catheter into said wall.

17. The method defined in claim 16 wherein said step of disposing further includes the step of forming a perforation in said wall prior to said step of ejecting.

18. The method defined in claim 17 wherein said step of disposing also includes the steps of ejecting a collapsed inflatable balloon with said stent into said wall from said distal end of said catheter, said stent surrounding said balloon, and inflating said balloon and opening said stent upon ejection of said balloon and said stent into said wall.

* * * * *

UNITED STATES PATENT AND TRADEMARK OFFICE
CERTIFICATE OF CORRECTION

PATENT NO.  : 5,409,019
DATED       : April 25, 1995
INVENTOR(S) : Peter J. Wilk It is certified that error appears in the above-indentified patent and that said Letters Patent is hereby corrected as shown below:

Column 3, line 47, delete "collapsed"; line 66, change "ventrical" to --ventricle--.

Column 4, line 38, insert --12-- after "stent".

Column 5, delete lines 59-68.

Column 6, delete lines 1 and 2; line 40, change "s tent" to --stent--.

Signed and Sealed this

Second Day of July, 1996

Attest:

BRUCE LEHMAN

*Attesting Officer*    *Commissioner of Patents and Trademarks*